US008731684B2

United States Patent
Carr et al.

(10) Patent No.: US 8,731,684 B2
(45) Date of Patent: May 20, 2014

(54) METHOD AND APPARATUS FOR ALIGNING AN ABLATION CATHETER AND A TEMPERATURE PROBE DURING AN ABLATION PROCEDURE

(75) Inventors: Kenneth L. Carr, Woolwich, ME (US); Robert C. Allison, Rancho Palos Verdes, CA (US)

(73) Assignee: Meridian Medical Systems, LLC, Portland, ME (US)

( * ) Notice: Subject to any disclaimer, the term of this patent is extended or adjusted under 35 U.S.C. 154(b) by 1345 days.

(21) Appl. No.: 12/356,205

(22) Filed: Jan. 20, 2009

(65) Prior Publication Data
US 2010/0185191 A1    Jul. 22, 2010

(51) Int. Cl.
*A61F 2/00* (2006.01)
*A61B 18/04* (2006.01)

(52) U.S. Cl.
USPC .............................. 607/102; 607/101; 606/33

(58) Field of Classification Search
USPC .......................................................... 604/33
See application file for complete search history.

(56) References Cited

U.S. PATENT DOCUMENTS

| | | | | |
|---|---|---|---|---|
| 4,346,716 A | * | 8/1982 | Carr ............................... | 600/407 |
| 4,813,429 A | * | 3/1989 | Eshel et al. ................... | 600/549 |
| 5,354,325 A | | 10/1994 | Chive et al. | |
| 5,683,382 A | | 11/1997 | Lenihan et al. | |
| 5,992,419 A | | 11/1999 | Sterzer et al. | |
| 6,477,426 B1 | | 11/2002 | Fenn et al. | |
| 2006/0106375 A1 | * | 5/2006 | Werneth et al. ................. | 606/32 |
| 2007/0055328 A1 | | 3/2007 | Mayse et al. | |
| 2007/0066968 A1 | | 3/2007 | Rahn | |
| 2007/0219548 A1 | | 9/2007 | Carr | |
| 2007/0299488 A1 | * | 12/2007 | Carr ............................... | 607/101 |
| 2009/0157067 A1 | * | 6/2009 | Kane et al. ....................... | 606/33 |

FOREIGN PATENT DOCUMENTS

| | | | | |
|---|---|---|---|---|
| EP | 0 485 323 A1 | | 5/1992 | |
| EP | 485323 A1 | * | 5/1992 | ............... A61N 5/02 |
| WO | WO 99/03535 A1 | | 1/1999 | |

OTHER PUBLICATIONS

"Notification of Transmittal of the International Search Report and the Written Opinion of the International Searching Authority, or the Declaration", International Application No. PCT/US2010/000129, filed Jan. 20, 2010, Date of Mailing May 7, 2010, 17 pages.

* cited by examiner

*Primary Examiner* — Jason Flick
*Assistant Examiner* — Weng Lee
(74) *Attorney, Agent, or Firm* — Cesari and McKenna, LLP

(57) ABSTRACT

Apparatus for aligning an ablation catheter and a temperature probe relatively for an ablation procedure includes an ablation catheter with a first antenna for ablating tissue at an ablation site in a patient's body and a temperature probe for placement in a body passage having a wall portion adjacent to the ablation site so that a second antenna in the probe is positioned opposite the first antenna. A microwave source provides a pulse modulated microwave signal to one of the antennas and a radiometer is in circuit with the other antenna. A synchronizing device in circuit with the microwave source and the radiometer enables the radiometer to synchronously detect the microwave signal so that the radiometer provides an alignment signal whose strength reflects the degree of alignment of the first and second antennas which signal may be used to control an alignment display. An alignment method using the apparatus is also disclosed.

20 Claims, 4 Drawing Sheets

METHOD AND APPARATUS FOR ALIGNING AN ABLATION CATHETER AND A TEMPERATURE PROBE DURING AN ABLATION PROCEDURE

BACKGROUND OF THE INVENTION

This invention relates generally to the treatment of certain diseases by tissue ablation wherein electromagnetic energy from an antenna in an ablation catheter heats tissue sufficiently to cause necrosis and a separate temperature sensing antenna in a temperature probe placed in a body passage or cavity adjacent to the ablation site measures tissue temperature to enable the operating surgeon to avoid overheating tissue during the ablation procedure. It relates especially to method and apparatus enabling the surgeon to align the two antennas to optimize that temperature measurement.

In a typical cardiac ablation procedure, an antenna catheter is used to resistively heat heart tissue, usually at the left side of the heart, sufficiently to intentionally damage the target tissue in order to cure a potentially fatal heart arrhythmia. Typically, heating the tissue to a temperature in excess of 70° C. for 30-60 seconds is sufficient to cause tissue necrosis. During treatment, electromagnetic energy, usually in the RF frequency range, is applied between the tip of the antenna catheter and a ground plate removably affixed to the patient's back, creating an electrical circuit. The point of highest resistance in this circuit, normally the interface between the catheter tip and the heart tissue, is the region which heats the most and thus may cause intentional, irreversible damage to the heart tissue to correct the arrhythmia.

Anatomically, the esophagus is very close to, and may even contact, part of the left atrium. Indeed, the average distance between the endocardial surface of the left atrium and the anterior surface of the esophagus is only in the order of 4.4+/−1.2 mm. Thus, ablating certain regions of the left atrium to treat various arrhythmias in the heart can unintentionally cause thermal damage to the esophagus, often with severe consequences.

In order to prevent such overheating, a temperature probe may be positioned in the patient's esophagus adjacent to the ablation site in the heart. One conventional temperature probe carries conventional point source temperature sensors such as thermocouples, thermistors or the like to monitor, and ultimately prevent the overheating of, the esophagus wall by cutting off or reducing the power delivered to the ablation catheter; see, e.g., US2007/0066968.

Another type of temperature probe developed only recently is disclosed in Provisional Application No. 61/145,800, of even date herewith, the entire contents of which are hereby incorporated herein by reference. That probe incorporates a microwave antenna which is connected to an external receiver in the form of a radiometer. The radiometer detects the thermal emissions picked up by the antenna in the probe which reflect the temperature of the tissue being examined and produces corresponding temperature signals to control a display which displays that temperature. During ablation, that apparatus can measure the temperature at depth in the esophageal tissue which is in close proximity to the ablation site in the patient's heart. That measurement can then be used to prevent unintentional thermal damage to the esophagus or other body passage.

As described in the above provisional application, a temperature probe using microwave radiometry provides definite advantages in that it can measure temperature at depth in the passage wall to avoid thermal damage thereto enabling the operating surgeon to adjust the power to the ablation catheter as needed to provide sufficient heating of the heart tissue to cause necrosis, but not enough to result in surface charring of that tissue that could cause a stroke and/or the formation of microbubbles (popping) that could rupture the heart vessel wall. Also, such radiometric sensing allows accurate measurement of tissue temperature even when cooling is being provided.

However, in order to optimize the accuracy of the temperature measurement provided by the temperature probe, it is desirable that the antenna therein be aligned properly with the antenna in the ablation catheter. Until now, there has been no means in the prior apparatus of this type to enable the operating surgeon to verify that the two antennas are indeed in alignment. Resultantly, in some instances, the temperature measurements may not be accurate enough to avoid thermal damage to tissue and in others, the ablation procedure may take too long because of tissue underheating.

SUMMARY OF THE INVENTION

Accordingly, an object of the present invention is to provide a method for properly aligning the antenna in an ablation catheter positioned at an ablation site in a human or animal body and the antenna in a temperature probe located in a body passage adjacent to the ablation site.

Another object is to provide such a method which can be employed even when the ablation site and/or passage are/is being cooled.

A further object is to provide apparatus for implementing the above method.

Still another object is to provide such apparatus wherein the antenna in the temperature probe may be either directional or omni-directional.

Other objects will, in part, be obvious and will, in part, appear hereinafter.

The invention accordingly comprises the several steps and the relation of one or more of such steps with respect to each of the others, and the apparatus embodying the features of construction, combination of elements and arrangement of parts which are adapted to effect such steps, all as exemplified in the following detailed description, and the scope of the invention will be indicated in the claims.

In apparatus of the type with which this invention is concerned, an ablation catheter containing a first antenna is positioned at an ablation site in a patient's body and a temperature probe containing a second antenna is placed in a body passage having a wall portion adjacent to the ablation site so that the probe is more or less opposite the ablation site. An electromagnetic signal of a first frequency may be delivered by an external generator to the first antenna to ablate tissue at the ablation site, while the second antenna picks up thermal emissions from said wall portion and provides a signal which may be detected and used to control a display so that the display indicates the temperature of that wall portion. By viewing the display, an operating surgeon can appropriately control the generator to avoid overheating the wall tissue.

In accordance with this invention, an antenna alignment circuit is connected between the two antennas. The alignment circuit includes a microwave source which transmits from one antenna to the other a modulated microwave signal of a second frequency different from the first frequency. That microwave signal is picked up by the other, receiving, antenna connected to a radiometer. The radiometer detects the microwave signal and produces an alignment signal whose strength is indicative of the degree of alignment of the first and second antennas. That is, the alignment signal is strongest when the two antennas are directly opposite one another. The alignment signal may be used to control a display enabling an operating surgeon to see exactly when the alignment signal strength is at a maximum signifying that the two antennas are in optimum alignment.

As we shall see, the microwave communication between the two antennas can be implemented in either direction to properly position the two antennas relatively both axially and in azimuth. The invention thus allows optimal delivery of ablation power to the antenna in the ablation catheter while preventing unwanted surface charring of the tissue being ablated and thermal damage to the passage wall adjacent to the ablation site. It will also allow the ablation procedure to be carried out in a minimum length of time.

Using this method, by observing the alignment display, a surgeon may determine in real time the relative position of an ablation catheter and a temperature probe and adjust one or the other to obtain the strongest alignment signal before the ablation procedure has commenced. Then, during the actual ablation when the RF energy from the ablation catheter starts to heat beyond the tissue intended to be heated and/or inadvertently starts to heat the wall of the adjacent body passage, e.g. the esophagus, there will be a noticeable temperature rise signaled by the temperature probe so that the apparatus' temperature display will provide the surgeon with a clear, early warning of potential tissue damage.

While we will describe the invention in a cardiac ablation context, the same antenna alignment technique may be used in connection with other procedures wherein tissue ablation is performed adjacent to a natural passage in the body, such as the treatment of benign prosthetic hyperplasia (BPH) wherein an ablation catheter is positioned in the patient's urethra and a temperature probe is located in the rectal cavity.

BRIEF DESCRIPTION OF THE DRAWINGS

For a fuller understanding of the nature and objects of the invention, reference should be made to the following detailed description taken in connection with the accompanying drawings, in which.

DESCRIPTION OF THE PREFERRED EMBODIMENTS

Figure 1:
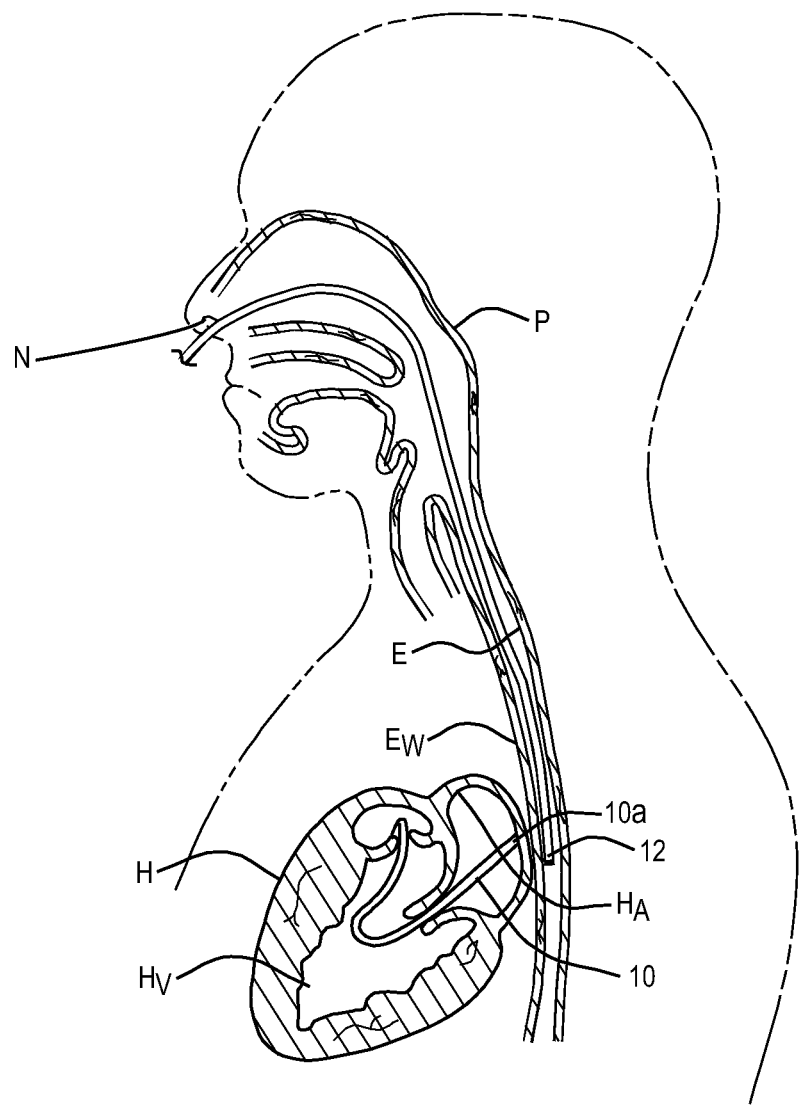
FIG. 1 is a diagrammatic view of a patient's head and torso showing an ablation catheter in the left atrium of the heart and a temperature probe situated in the esophagus adjacent to the catheter.

Refer first to FIG. 1 of the drawings which shows the head and torso of a patient having a heart H with a left ventricle $H_V$ and a left atrium $H_A$. As is usually the case, the left atrium of the heart is very close to the anterior wall of the patient's esophagus E. During a conventional cardiac ablation procedure, an ablation catheter 10 is threaded into the left atrium $H_A$ via left ventricle $H_V$ so that the working end 10a of the catheter contacts the posterior wall of the left atrium as shown in FIG. 1.

In order to prevent overheating of the esophagus E during such an ablation procedure, a temperature probe 12 may be inserted into the patient's nasal passage N and threaded down into the esophagus E via the patient's pharynx P until the probe is positioned directly opposite the catheter end 10a at the ablation site as shown in FIG. 1. As the heart tissue is being ablated by catheter 10, the temperature probe 12 picks up thermal emissions from the esophageal wall $E_W$ and corresponding temperature signals are produced which may be used to prevent overheating of the esophagus as described in detail in the above provisional application.

Figure 2:
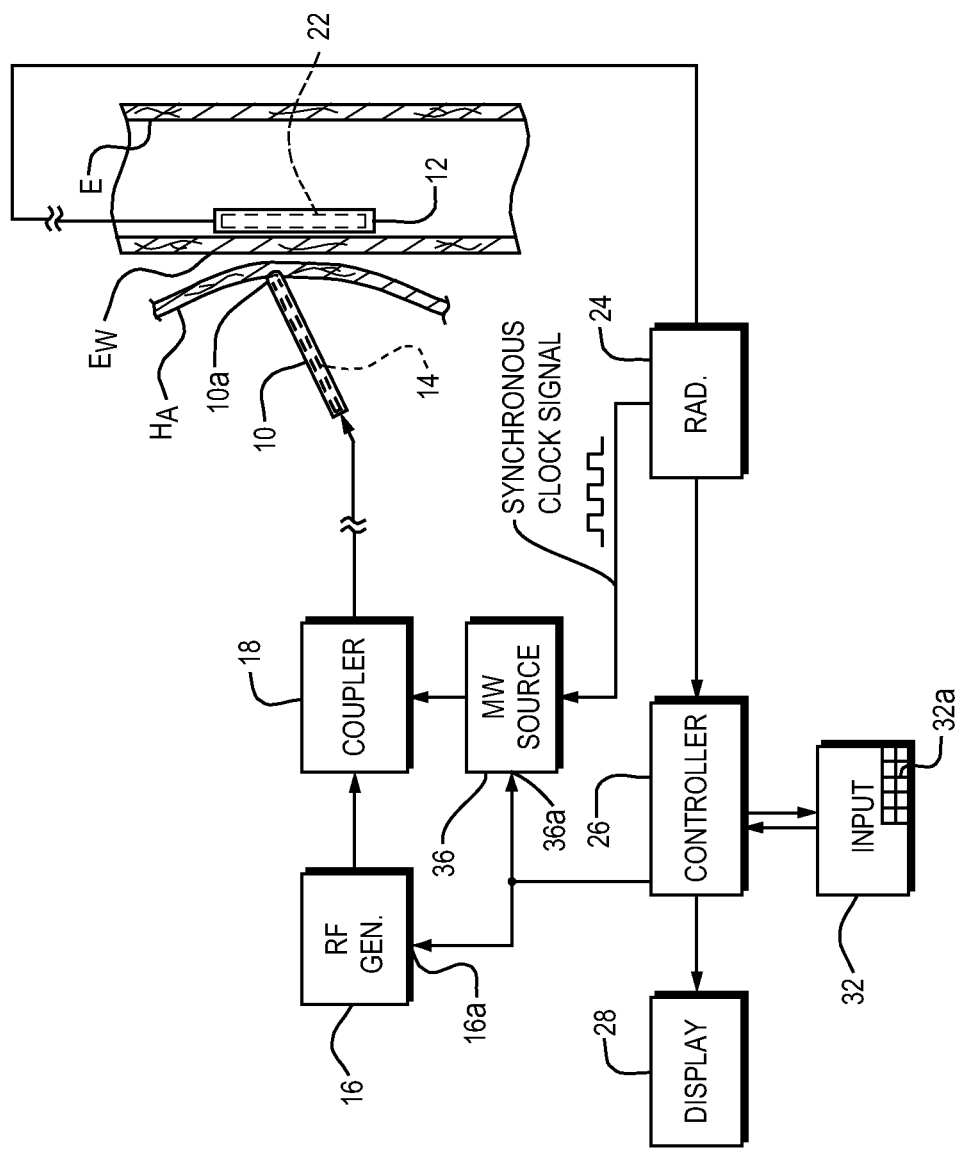
FIG. 2 is a block diagram of apparatus for aligning an ablation catheter and a temperature probe according to this invention.

Referring to FIG. 2, catheter 10 includes an ablation antenna 14 which receives an RF signal from an RF generator 16. Preferably, antenna 14 is of the type disclosed in US2007/0299488, the contents of which are hereby incorporated herein by reference and it is matched to a selected first frequency, e.g. 550 KHz. However, instead of receiving this signal from the generator directly, the antenna receives it by way of a microwave coupler 18 which is part of an alignment circuit to be described in detail shortly.

The temperature probe 12 contains an antenna 22 for picking up thermal emissions from the wall portion $E_W$. Preferably, the antenna is of the type described in US2007/0219548, the contents of which are hereby incorporated herein by reference. Antenna 22 is connected to the input of a radiometer 24 which detects the signal from antenna 22 and produces a corresponding temperature signal. Preferably, the radiometer operates at a center frequency corresponding to a second frequency, i.e. 4.0 GHz, so that the apparatus can detect thermal emissions from relatively deep regions of the esophageal wall $E_W$.

The temperature signal from the radiometer is routed to a controller 26 which produces a corresponding control signal for controlling a display 28 which can display the temperature of the tissue being examined by the probe 12. Preferably, the display indicates esophageal tissue temperature as a function of time so that the surgeon can see that temperature in real time. Of course, the display 28 may also display other parameters relating to proper operation of the apparatus.

The controller 26 may receive instructions via the control buttons 32a of an operator-controlled input keyboard 32.

As described in the above provisional application, the temperature signal from controller 26 may also be coupled to a control input terminal 16a of the generator 16 to control the power being delivered to the ablation catheter 10 and the apparatus may include means for cooling the tissue at the ablation site and/or the esophagus.

Still referring to FIG. 2, the alignment circuit mentioned above is provided in order to assure that the antenna 22 in probe 12 is aligned with the antenna 14 in catheter 10 when the ablation procedure is carried out to allow optimal delivery of ablation power to the antenna 14 with minimal likelihood of unwanted thermal damage to the heart and/or to the esophageal wall $E_W$ during the ablation procedure.

The alignment circuit comprises, in addition to the coupler 18, a microwave source 36 controlled by a clock signal from radiometer 24 so that the radiometer and source 36 operate in synchronism. The source 36 provides a signal of a second frequency different from the first, e.g. 4.0 GHz, which is pulse modulated. This microwave signal from source 36 is coupled to, and transmitted by, antenna 14, picked up by antenna 22 and detected by radiometer 24. Modulation of the transmitted waveform allows detection by the radiometer 24 of very low levels of microwave signal in the presence of high levels of interfering noise. Thus, the AM pulse modulated microwave signal from antenna 14 can easily be recognized and detected by the sensitive radiometer 24 and the strength of this signal is directly related to the degree of alignment of the two antennas. In response to the detected signal, the radiometer delivers an alignment signal via controller 26 to display 28 which thereupon provides an indication of that signal strength as a function of time.

Preferably, the two antennas 14 and 22 are aligned prior to the actual ablation procedure. For this, the controller 26 may be instructed via terminal 32 or a hand control (not shown) on catheter 10 to apply a control signal C to the control terminal 16a of generator 16 that turns off or reduces the RF power output from the generator for a selected time or until the operator determines from the display 28 that the antennas are aligned following which the signal C from the controller may cause the generator to operate at full power sufficient to ablate tissue. That same control signal C is applied to a control terminal 36a of source 36 to deactivate that source so that the generator and source are active alternatively.

The antenna 22 in temperature probe 12 may be omnidirectional, but is more preferably a directional antenna of the type described in the above US2007/0299488. Such a directional antenna provides a better temperature measurement resolution in the direction of the catheter 10. That is, with a directional antenna, the tissue at wall portion $E_W$ represents a more significant portion of the antenna pattern of antenna 12, which will significantly improve the temperature measurement resolution.

The microwave coupler 18 in the FIG. 2 apparatus may have different forms. Preferably, it is located near the proximal end of catheter 10 and near the generator 16. The coupler is basically a diplexer or T/R switch which couples the microwave signal from source 36 to antenna 14. A capacitive coupling method is preferred, with a directional capacitive coupling approach being the optimum. This approach directs the microwave energy from source 36 toward the antenna 14 and away from the RF generator 16. The modulated microwave signal propagates out to the tip of antenna 14 where it radiates into the heart tissue.

Figure 3A:
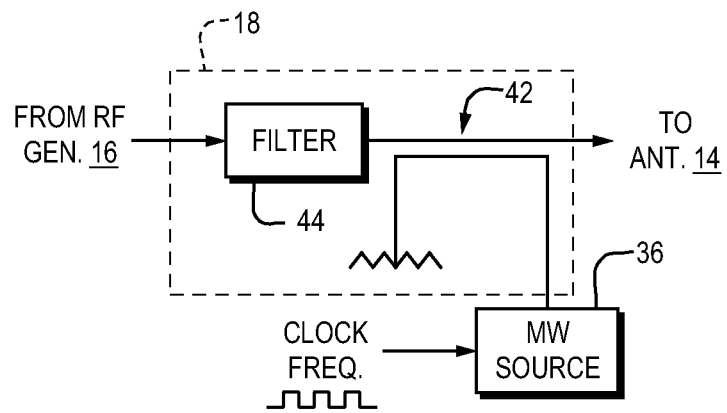
FIGS. 3A to 3C are diagrammatic views showing different versions of the coupler portion of the FIG. 2 apparatus.

In the coupler 18 depicted in FIG. 3A, the signal from microwave source 36 is capacitively coupled at 42 to the line from RF generator 16 to antenna 14 with an upstream filter 44 being provided which passes the RF signal but isolates generator 16 from the microwave signal.

Figure 3B:
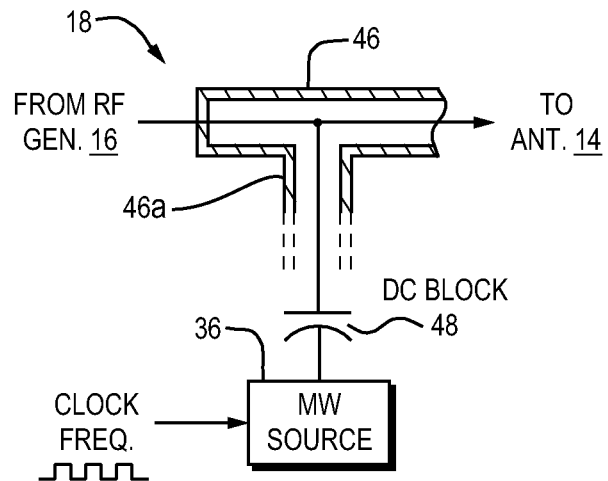

In FIG. 3B, the coupler 18 comprises a transmission line 46 connected between generator 16 and antenna 14, with a branch 46a receiving the output signal from source 36 by way of a DC blocking capacitor 48.

Figure 3C:
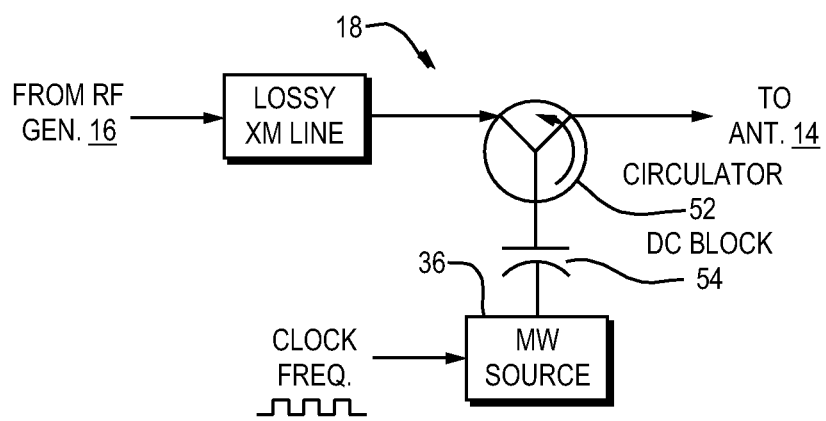

In FIG. 3C, the coupler 18 comprises a conventional ferrite circulator 52 connected between generator 16 and antenna 14 and designed to operate at said second selected frequency, i.e, 4.0 GHz. The circulator center conductor provides a conductive path that connects the RF generator 16 to antenna 14. The signal from microwave source 36 is applied to the circulator by way of a DC blocking capacitor 54.

In use, the temperature probe 12 is normally inserted through the nose and down into the esophagus. With the apparatus operating in an alignment mode, the probe antenna 22 is aligned with antenna 14 in the ablation catheter 10 by varying its position in the esophagus to maximize the received alignment signal strength as indicated by display 28. Rotating the probe 12 and its antenna 22 steers the antenna pattern in an azimuth direction while insertion and retraction of the probe shifts the antenna pattern in an axial direction. The probe 12 is optimally positioned for detection of dangerous ablation temperatures when the two antennas 14 and 22 are in closest proximity as indicated by display 28 displaying a maximum received signal strength.

Following alignment, the apparatus may be switched to its ablation mode with generator 16 delivering sufficient power to antenna 14 to ablate tissue. Thus, alignment of the two antennas is usually, but not necessarily, carried out during an alignment phase prior to the actual ablation procedure while generator 16 is delivering zero or sublethal power to antenna 14.

Figure 4:
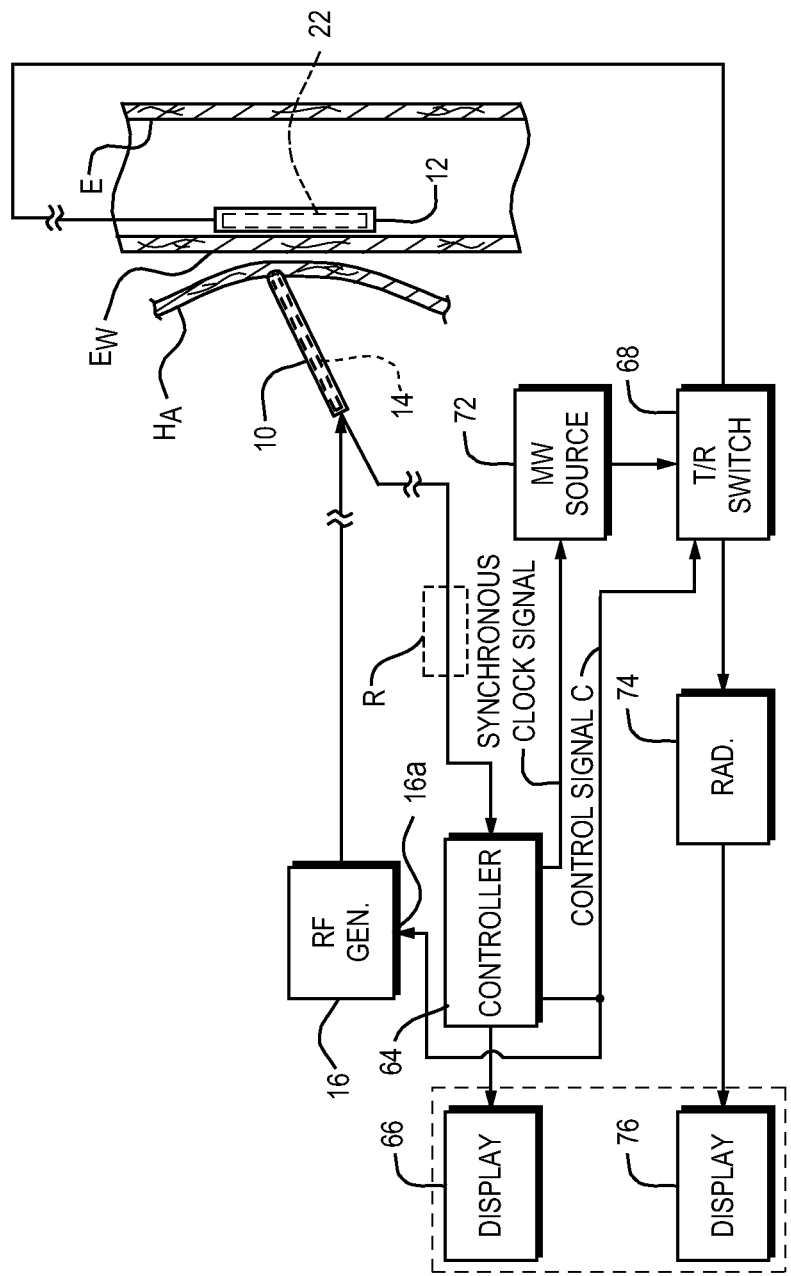
FIG. 4 is a diagram similar to FIG. 2 of a second embodiment of the invention.

In the FIG. 2 embodiment of the invention, the catheter antenna 14 transmits a signal to probe antenna 22 to effect antenna alignment. However, the opposite may be the case as shown in FIG. 4. In the FIG. 4 apparatus, the catheter 10 is preferably of the type described in the above US2007/0299488 having a radiometer incorporated right in the catheter 10 along with the antenna 14, albeit the radiometer could just as well be outside the catheter as shown in phantom at R in FIG. 4. In either event, antenna 14 receives an RF signal from a generator 16 to ablate tissue as before. Here, the primary function of the radiometer in catheter 10 (or radiometer R) is to monitor the ablation temperature in the heart atrium $H_A$. For this, the radiometer detects thermal emissions picked up by antenna 14 and produces a signal which is fed to a radiometer controller 64 that controls a display 66. As in the FIG. 2 apparatus, instructions to controller 64 may be input via a keyboard (not shown).

The FIG. 4 apparatus also includes a temperature probe 12 containing an antenna 22 similar to the one in FIG. 2. A T/R switch 68 or equivalent connects antenna 22 either to a microwave source 72 similar to source 36 or to a radiometer 74 whose output controls a display 76 which may be combined with display 66.

A clock signal from the radiometer is applied by way of controller 64 to the microwave source 72 so that radiometer in catheter 10 (or radiometer R) and source 72 operate in synchronism.

Like the FIG. 2 apparatus, the FIG. 4 instrument may be operated in an alignment mode prior to the ablation procedure. For this, controller 64 may be instructed to output a control signal C to generator 16 which turns off the generator and to switch 68 which connects microwave source 72 to the antenna 22 in probe 12, while isolating the radiometer 74. Antenna 22 will thereupon transmit a pulse modulated microwave signal to the antenna 14 which is detected by the radiometer in ablation catheter 10 (or radiometer R). That radiometer will then deliver an alignment signal to controller 64. The controller controls display 66 so that the latter displays an amplitude modulated signal whose strength is indicative of the degree of alignment of the two antennas 14 and 22.

After the alignment step whose duration may be input by the operator, timed by controller 64 or based on a selected parameter, e.g. a selected maximum alignment signal strength, the controller may activate RF generator 16 and switch 68 so that the antenna 22 in probe 12 is disconnected from source 72 and coupled to radiometer 74. That radiometer may thereupon provide a temperature signal to display 76 so that the temperature of the esophagus wall portion $E_W$ can be seen by the operating surgeon in real time. The surgeon may then control generator 16 as needed to avoid overheating the esophagus.

As noted above, the present method and apparatus are applicable not only to align the ablation and temperature sensing antennas during a cardiac ablation procedure, they can be used whenever two antennas have to be aligned on opposite sides of any body passage wall. In all cases, our method and apparatus, which utilize an AM pulse modulated microwave signal with synchronous detection allows optimal alignment of the two antennas because it provides high sensitivity and very good noise immunity under normal operating room conditions.

It will thus be seen that the objects set forth above, among those made apparent from the preceding description, are efficiently attained and, since certain changes may be made in carrying out the above method and in the constructions set forth without departing from the scope of the invention, it is intended that all matter contained in the above description or shown in the accompanying drawings shall be interpreted as illustrative and not in a limiting sense.

It is also to be understood that the following claims are intended to cover all the generic and specific features of the invention described herein.

What is claimed is:

1. Apparatus for aligning an ablation catheter and a temperature probe relatively for an ablation procedure, said apparatus comprising
    an ablation catheter for ablating tissue at an ablation site in a patient's body, said catheter including a heating antenna;
    a temperature probe containing a heat sensing antenna and for placement in a body passage having a wall portion adjacent to the ablation site so that said heat sensing antenna is positioned opposite the heating antenna;
    a microwave source providing a pulse modulated microwave signal to one of said antennas, said modulated microwave signal being picked up by the other of said antennas;
    a radiometer having an input in circuit with the other of said antennas and an output;
    a synchronizing device in circuit with said source and said radiometer enabling the radiometer to synchronously detect said modulated microwave signal so that the radiometer output can provide an alignment signal whose strength reflects the degree of alignment of said antennas, and
    a generator for delivery power to said heating antenna to heat the tissue whereby the tissue emits thermal radiation which is picked up by the heat sensing antenna.

2. The apparatus defined in claim 1 wherein
    said one antenna is the heating antenna;
    a microwave coupler is in circuit between said microwave source and said heating antenna, and
    the synchronizing device delivers clock pulses from the radiometer to the microwave source to synchronize their operations.

3. The apparatus defined in claim 2 wherein the coupler comprises a directional capacitive coupling device and a filter in circuit between the coupling device and the generator.

4. The apparatus defined in claim 2 wherein the coupler comprises a diplexer.

5. The apparatus defined in claim 2 wherein the coupler comprises a ferrite circulator.

6. The apparatus defined in claim 5 wherein the coupler further includes a lossy transmission line connected between the circulator and the generator and a capacitor connected between the circulator and an output of the microwave source.

7. The apparatus defined in claim 2 and further including
    a control device controlling the operations of the generator and microwave source in a mutually exclusive fashion so that the when the microwave source is operative, said radiometer output provides said alignment signal and when the generator is operative to ablate tissue, the radiometer output provides a temperature signal indicating the temperature of said wall portion.

8. The apparatus defined in claim 7 and further including a display device connected to the radiometer output.

9. The apparatus defined in claim 1 wherein
    said one of the antennas is the heat sensing antenna;
    the microwave source provides the modulated microwave signal to the heat sensing antenna, and
    the radiometer input is in circuit with the heating antenna.

10. The apparatus defined in claim 9 wherein the radiometer is located in the ablation catheter.

11. The apparatus defined in claim 7 and further including
    a second radiometer having an input and an output;
    a switching device connected between the heat sensing antenna and the input of the second radiometer, said modulated microwave signal being applied to the heat sensing antenna by way of said switching device,
    said control device controlling the operations of the generator and the switching device so that when the generator is operative, the switching device connects the microwave source to the heat sensing antenna and when the generator is not operative, the switching device connects the heat sensing antenna to the input of the second radiometer.

12. The apparatus defined in claim 11 and further including a display device responsive to said alignment signal so that the display device displays the strength of the alignment signal.

13. The apparatus defined in claim 12 and further including a second display device responsive to said temperature signal so that the second display device displays the temperature of said wall portion.

14. A method of aligning an ablation catheter and a temperature probe for an ablation procedure comprising the steps of
    placing an ablation catheter containing a heating antenna at an ablation site in a patient's body;
    positioning a temperature probe containing a heat sensing antenna in a body passage having a wall portion adjacent to the ablation site so that the heat sensing antenna is positioned opposite the heating antenna;
    applying a pulse modulated microwave signal to one of said antennas so that said signal is picked up by the other of said antennas;
    synchronously detecting the modulated microwave signal picked up by said other of said antennas to provide an alignment signal whose strength reflects the degree of alignment of said antennas using a radiometer having an input in circuit with the other of said antennas and an output, and
    delivering power to the heating antenna to heat the tissue after maximizing the strength of the alignment signal by repositioning the catheter and/or the probe as necessary, whereby said tissue emits thermal radiation which is picked up by the heat sensing antenna.

15. The method defined in claim 14 including the additional step of applying the alignment signal to a display device to display the corresponding signal strength.

16. The method defined in claim 15 including the steps of
    applying the modulated microwave signal to the heating antenna, and
    synchronously detecting the modulated microwave signal picked up by the heat sensing antenna.

17. The method defined in claim 14 including the steps of
    applying the modulated microwave signal to the heat sensing antenna, and
    synchronously detecting the modulated microwave signal picked up by the heating antenna.

18. The method defined in claim 17 wherein the microwave signal is detected by a radiometer located in the ablation catheter.

19. The method defined in claim 14 including the additional steps of detecting the radiation picked up by the heat sensing antenna to provide a corresponding temperature signal, and controlling the applying and delivering steps so that they are operative in the alternative.

20. The method defined in claim 19 including the additional step of applying the temperature signal to a display device to display the corresponding temperature.

\* \* \* \* \*